United States Patent
Marchán Sancho et al.

(10) Patent No.: US 11,672,798 B2
(45) Date of Patent: Jun. 13, 2023

(54) CIPROFLOXACIN OPHTHALMIC TOPICAL COMPOSITION FOR TREATING OCULAR DISEASE

(71) Applicant: LABORATORIOS SALVAT, S.A., Esplugues de Llobregat (ES)

(72) Inventors: Sandra Marchán Sancho, Esplugues de Llobregat (ES); Francisca Toribio Santisteban, Esplugues de Llobregat (ES); María Isabel Delgado Gañán, Barcelona (ES)

(73) Assignee: LABORATORIOS SALVAT, S.A., Esplugues de Llobregat (ES)

( * ) Notice: Subject to any disclaimer, the term of this patent is extended or adjusted under 35 U.S.C. 154(b) by 0 days.

(21) Appl. No.: 17/561,631

(22) Filed: Dec. 23, 2021

(65) Prior Publication Data
US 2022/0387422 A1 Dec. 8, 2022

(30) Foreign Application Priority Data
Jun. 3, 2021 (EP) .................................... 21382493

(51) Int. Cl.
*A61K 31/496* (2006.01)
*A61K 9/00* (2006.01)
*A61K 31/573* (2006.01)

(52) U.S. Cl.
CPC .......... *A61K 31/496* (2013.01); *A61K 9/0048* (2013.01); *A61K 31/573* (2013.01)

(58) Field of Classification Search
None
See application file for complete search history.

(56) References Cited

U.S. PATENT DOCUMENTS

| | | | | |
|---|---|---|---|---|
| 2010/0285151 A1* | 11/2010 | Goldan | .................. | A61P 31/04 424/662 |
| 2011/0212932 A1* | 9/2011 | Ruiz I Pol | ............. | A61K 31/58 514/171 |
| 2017/0049786 A1* | 2/2017 | Nivaggioli | .............. | A61P 27/02 |
| 2018/0333414 A1* | 11/2018 | Musunuri | ............ | A61K 9/1075 |

FOREIGN PATENT DOCUMENTS

EP 2366408 7/2012

OTHER PUBLICATIONS

Lorente et al., Ciprofloxacin plus fluocinolone acetonide versus ciprofloxacin alone in the treatment of diffuse otitis externa, The Journal of Laryngology & Otology (2014), 128, 591-598. (Year: 2014).*
Extended European Search Report (EESR) for EP Application No. 21382493.1, dated Nov. 3, 2021, 7 pages.
Ke Tai-Lee et al., "Ocular bioavailability of ciprofloxacin in sustained release formulations", Journal of Ocular Pharmacology and Therapeutics, Mary Ann Liebert, Inc. New York, vol. 17, No. 6, Dec. 1, 2001, pp. 555-563.
Engel et al., "Effectiveness of Specific Antibiotic/Steroid Combinations for Therapy of Experimental Pseudomonas Aeruginosa Keratitis" Current Eye Research, Informa Healthcare, vol. 14, No. 3, Jan. 1, 1995, pp. 229-234.
Kadmiel M. et al., "Glucocorticoid action in human corneal epithelial cells establishes roles for corticosteroids in wound healing and barrier function of the eye", Experimental Eye Research, 2016, vol. 152, pp. 10-33.
Fleiszig S.M. et al, "Pseudomonas aeruginosa invades corneal epithelial cells during experimental infection", Infection and Immunity, 1994, vol. 62(8), pp. 3485-3493.
Cetraxal® (ciprofloxacin otic solution), NDA 21-918, Apr. 2009, Prescribing Information, Food and Drug Administration (FDA), 8 pages.
Ciloxan® (ciprofloxacin ophthalmic solution), NDA 19992/S-026, 2016, Reference ID 4072618, pp. 3-8.
Hefelfinger: "Inclusion Blennorrhea of the Newborn", Clinical Pediatrics 1978; vol. 17(7), pp. 279-280.

* cited by examiner

*Primary Examiner* — Jennifer A Berrios
(74) *Attorney, Agent, or Firm* — Squire Patton Boggs (US) LLP

(57) ABSTRACT

The present invention provides a combination comprising ciprofloxacin, or a pharmaceutically acceptable salt thereof, and fluocinolone acetonide for use in the prevention and/or treatment of an ocular disease, wherein the prevention and/or treatment comprises the topical administration of the combination. The invention also provides an ophthalmic topical pharmaceutical composition comprising the combination together with at least one ophthalmically acceptable excipient, diluent, or carrier, for use in the prevention and/or treatment of an ocular disease, wherein the prevention and/or treatment comprises the topical administration of the composition.

14 Claims, 5 Drawing Sheets

CIPROFLOXACIN OPHTHALMIC TOPICAL COMPOSITION FOR TREATING OCULAR DISEASE

TECHNICAL FIELD

The present invention relates to the field of medicine. In particular, it relates to compositions for the topical treatment of ocular diseases. The compositions of the invention are particularly useful for the treatment of antibiotic-resistant eye infections.

BACKGROUND ART

Ciprofloxacin, a fluoroquinolone antibacterial agent, is active against a broad spectrum of gram-positive and gram-negative bacteria. It acts by inhibition of topoisomerase II (DNA gyrase) and topoisomerase IV, which are enzymes required for bacterial replication, transcription, repair, and recombination.

Despite its antimicrobial properties, systemic administration of ciprofloxacin does produce bothersome side effects, such as gastrointestinal intolerance (vomiting, diarrhoea, abdominal discomfort), as well as dizziness, insomnia, irritability, and increased levels of anxiety. Thus, topical application of ciprofloxacin is highly preferred because of the ease of administration, lack of associated complications and minimal non-specific systemic exposure.

However, topical administration of ciprofloxacin is very challenging in specific tissues, such as the eye. A number of physiological and anatomical constraints of the ocular tissue generally results in a very low bioavailability of topically applied ciprofloxacin compositions. The main causes of this poor bioavailability are the very low permeability of the corneal epithelial membrane, lacrimation, tear turnover, tear dilution and conjunctival absorption. In fact, only around 1% of the topically instilled drug is absorbed into the ocular tissue.

This has caused that currently marketed ciprofloxacin ophthalmic solutions often need complicated and arduous dosing regimens that can lead to poor patient compliance, which, in turn, ultimately contributes to poor therapeutic outcomes and other complications.

Moreover, the low intracellular antibiotic concentrations achieved by current ophthalmic ciprofloxacin solutions limits their activity, in particular against antibiotic-resistant bacteria, and are easily circumvented by bacterial antibiotic-tolerance mechanisms based on cellular internalization. Infectious diseases caused by intracellular bacteria present a significant challenge to antibiotic therapy. Antibiotic treatment of these types of infections has been associated with high failure and/or relapse rates.

Internalization of bacteria in cells is a well described mechanism of protection against the antibiotics present in the extracellular environment, being one of the major causes of failure of conventional antibiotic therapies (Fleiszig S. M. et al, "*Pseudomonas aeruginosa* invades corneal epithelial cells during experimental infection", Infect Immun, 1994, vol. 62(8), pp. 3485-93). The low penetration of antibiotics inside the cells is an additional factor involved in this limited efficacy; therefore, strategies that increase the intracellular level of antibiotics will consequently improve the therapeutic efficacy. Thus, there is a clear need for alternative ophthalmic topical ciprofloxacin compositions with enhanced penetration capacity into the ocular tissues.

SUMMARY OF INVENTION

The present inventors have surprisingly found that fluocinolone acetonide is capable of increasing the ocular tissue penetration of topically applied ciprofloxacin.

As shown in the examples below, the inventors found that addition of fluocinolone acetonide to a ciprofloxacin solution highly increased its cellular permeability into corneal cells. This penetration enhancing effect was dose-dependent —the higher the concentration of fluocinolone acetonide added, the higher the concentration of intracellular ciprofloxacin detected. Moreover, comparative analysis with dexamethasone and hydrocortisone sodium phosphate, which are two of the most widely used ophthalmic corticosteroids, confirmed that this effect was highly specific for fluocinolone acetonide. As shown in FIG. 1 to FIG. 5, for all corticosteroid concentrations tested, intracellular levels of ciprofloxacin were higher when fluocinolone acetonide was added to the cell medium. Neither dexamethasone nor hydrocortisone sodium phosphate promoted the absorption of ciprofloxacin into the cells; which reinforces that the observed positive action of fluocinolone acetonide is a specific and unexpected activity of this molecule.

The positive effect of fluocinolone acetonide on ciprofloxacin ocular bioavailability was highly unexpected in view of the prior art as it has been extensively described that corticosteroids decrease cell permeability through various mechanisms, such as tight-junction potentiation, also in corneal epithelium (Kadmiel M. et al., "Glucocorticoid action in human corneal epithelial cells establishes roles for corticosteroids in wound healing and barrier function of the eye", Exp Eye Res., 2016, vol. 152, pp. 10-33). Moreover, as it was also known that corticosteroids have the undesirable side effect of limiting the body's intrinsic ability to fight infection, it was not expected that a particular corticosteroid could enhance the efficiency of ciprofloxacin against bacterial infection, in particular against intracellular bacteria.

Thus, the combination of ciprofloxacin and fluocinolone acetonide herein provided is highly useful for treating ophthalmic disorders given the higher penetration capacity of the antibiotic into the ocular tissue. Furthermore, the high levels of intracellular ciprofloxacin achieved by the combination of the invention constitutes a great step forward in the field of ophthalmic topical antibiotic treatments as it allows treating ocular antibiotic-resistant bacterial infections, which required higher intracellular antibiotic concentrations, and it also helps to prevent the bacterial antibiotic-tolerance mechanisms based on cellular internalization.

Therefore, in a first aspect, the present invention provides a combination comprising ciprofloxacin, or a pharmaceutically acceptable salt thereof, and fluocinolone acetonide for use in the prevention and/or treatment of an ocular disease, wherein the prevention and/or treatment comprises the topical administration of the combination.

This aspect can also be formulated as the use of the combination of the first aspect for the manufacture of a medicament for the prevention and/or treatment of an ocular disease, wherein the prevention and/or treatment comprises the topical administration of the medicament. This aspect can also be formulated as a method for preventing and/or treating an ocular disease, the method comprising topically administering a therapeutically effective amount of ciprofloxacin, or a pharmaceutically acceptable salt thereof, and a therapeutically effective amount of fluocinolone acetonide, together with ophthalmologically acceptable excipients, diluents, or carriers to a subject in need thereof.

In a second aspect, the present invention provides ciprofloxacin, or a pharmaceutically acceptable salt thereof, for use in the prevention and/or treatment of an ocular disease by topical administration, wherein the ciprofloxacin, or the pharmaceutically acceptable salt thereof, is for use in combination therapy with fluocinolone acetonide.

In a third aspect, the present invention provides fluocinolone acetonide for use in the prevention and/or treatment of an ocular disease by topical administration, wherein the fluocinolone acetonide is for use in combination therapy with ciprofloxacin, or a pharmaceutically acceptable salt thereof.

In a fourth aspect, the present invention provides an ophthalmic topical pharmaceutical composition comprising a therapeutically effective amount of ciprofloxacin, or a pharmaceutically acceptable salt thereof, and a therapeutically effective amount of fluocinolone acetonide, together with at least one ophthalmically acceptable excipient, diluent, or carrier, for use in the prevention and/or treatment of an ocular disease, wherein the prevention and/or treatment comprises the topical administration of the composition.

This aspect can also be formulated as the use of the composition of the fourth aspect for the manufacture of a medicament for the prevention and/or treatment of an ocular disease, wherein the prevention and/or treatment comprises the topical administration of the medicament. This aspect can also be formulated as a method for preventing and/or treating an ocular disease in a subject in need, the method comprising topically administering a therapeutically effective amount of the composition of the fourth aspect to a subject in need thereof.

DETAILED DESCRIPTION OF THE INVENTION

Figure 1:
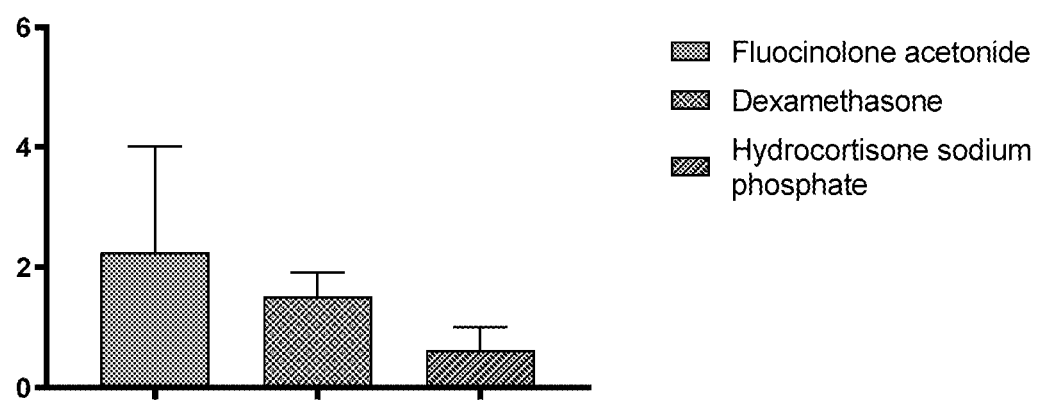
FIG. 1 shows the intracellular concentration of ciprofloxacin (ng/ml) in corneal epithelial cells, determined by ultra-high-performance liquid chromatography coupled to tandem mass spectrometry (UHPLC-MS/MS), following 15 minutes of incubation with different corticosteroids at 2.8 µg/ml and ciprofloxacin at 20 µg/ml. Data was normalized to the control sample (intracellular levels of ciprofloxacin in the absence of corticosteroids) by subtracting for each assay the value of the control. Results are expressed as means±S.E.M of three independent experiments. The y-axis represents the intracellular concentration of ciprofloxacin (ng/ml), and the x-axis represents the tested corticosteroid at 2.8 µg/ml.

All terms as used herein in this application, unless otherwise stated, shall be understood in their ordinary meaning as known in the art. Other more specific definitions for certain terms as used in the present application are as set forth below and are intended to apply uniformly throughout the specification and claims unless an otherwise expressly set out definition provides a broader definition.

As used herein, the indefinite articles "a" and "an" are synonymous with "at least one" or "one or more." Unless indicated otherwise, definite articles used herein, such as "the" also include the plural of the noun.

The term "weight/volume percentage" refers to the weight in grams of a compound per 100 ml of composition. It is represented as % w/v along the description, or only as %.

As described above, in a first aspect the present invention provides a combination comprising ciprofloxacin, or a pharmaceutically acceptable salt thereof, and fluocinolone acetonide for use in the prevention and/or treatment of an ocular disease, wherein the prevention and/or treatment comprises the topical administration of the combination. In a second and third aspects, the invention provides ciprofloxacin or fluocinolone acetonide for use in combination therapy with fluocinolone acetonide or ciprofloxacin, respectively, for the prevention and/or treatment of an ocular disease. This means that the prevention and/or treatment of and ocular disease involves the topical use of ciprofloxacin and indications for the use in combined therapy with fluocinolone acetonide, or alternatively, the topical use of fluocinolone acetonide and indications for the use in combined therapy with ciprofloxacin.

The invention also provides a combination comprising ciprofloxacin, or a pharmaceutically acceptable salt thereof, and a penetration enhancer, for use in the prevention and/or treatment of an ocular disease, wherein the prevention and/or treatment comprises the topical administration of the combination, and wherein the penetration enhancer is fluocinolone acetonide. Thus, in the combination of the invention the ciprofloxacin and the fluocinolone acetonide act synergistically to increase the antibacterial activity of ciprofloxacin by enhancing its cellular penetration capacity.

As used herein, the term "ocular disease" refers to any disease or disorder of the eye or pertaining to the eye, in particular, infections thereof.

In a particular embodiment of the first aspect, optionally in combination with any of the embodiments provided above or below, the combination is administered in the form of an ophthalmic topical pharmaceutical composition together with at least one ophthalmically acceptable excipient, diluent, or carrier.

In a particular embodiment of the combination of the first aspect, optionally in combination with any of the embodiments provided above or below, the prevention and/or treatment comprises the topical administration to a subject:
either
(a) an ophthalmic topical pharmaceutical composition comprising:
a therapeutically effective amount of ciprofloxacin, or a pharmaceutically acceptable salt thereof; and
a therapeutically effective amount of fluocinolone acetonide;
together with one or more ophthalmically acceptable excipients, diluents, or carriers;
or alternatively,
(b) simultaneously, sequentially, or separately:
(b1) an ophthalmic topical pharmaceutical composition comprising a therapeutically effective amount of ciprofloxacin, or a pharmaceutically acceptable salt thereof; together with one or more pharmaceutically acceptable excipients, diluents, or carriers; and
(b2) an ophthalmic topical pharmaceutical composition comprising a therapeutically effective amount of fluocinolone acetonide;
together with one or more ophthalmically acceptable excipients, diluents, or carriers.

"Ciprofloxacin" refers to a compound with CAS number 85721-33-1 and of formula (I):

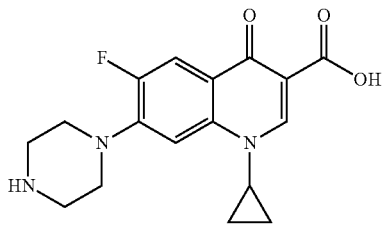

(I)

Ciprofloxacin is a synthetic broad spectrum fluoroquinolone antibiotic. The primary mode of action is inhibition of the bacterial DNA-gyrase and topoisomerase IV enzymes. The molecular formula for ciprofloxacin is $C_{17}H_{18}FN_3O_3$. Ciprofloxacin can be in the form of a pharmaceutically acceptable salt. The term "pharmaceutically acceptable salt" used herein encompasses a salt formed from pharmaceutically acceptable non-toxic acids including inorganic or organic acids. There is no limitation regarding the salts, except that if used for therapeutic purposes, they must be pharmaceutically acceptable. Salts of ciprofloxacin may be prepared from pharmaceutically acceptable non-toxic acids, including inorganic and organic acids. Such acids include among others acetic, adipic, benzene sulfonic, benzoic, camphor sulfonic, citric, ethanesulfonic, fumaric, gluconic, glutamic, hydrobromic, hydrochloric, lactic, maleic, malic, mandelic, methanesulfonic, phosphoric, succinic, sulphuric, tartaric, and p-toluensulfonic acid. Salts of ciprofloxacin may also be prepared from pharmaceutically acceptable non-toxic quaternary amines, including among others choline, methylimidazolium derivatives, and cetylpyridinium. Ciprofloxacin and the salts of ciprofloxacin may be in crystalline form either as free solvation compounds or as solvates (e.g., hydrates) and it is intended that both forms are within the scope of the present invention. Methods of solvation are generally known within the art. As above exposed particular solvates include hydrated forms, more in particular mono- and dihydrated forms of ciprofloxacin. Thus, the present invention is meant to encompass hydrated forms of ciprofloxacin and hydrated forms of ciprofloxacin salts.

In a particular embodiment of the combination of the first, second, third, and fourth aspects, optionally in combination with any of the embodiments provided above or below, the ciprofloxacin salt is ciprofloxacin hydrochloride.

In a particular embodiment of the combination of the first, second, third, and fourth aspects, optionally in combination with any of the embodiments provided above or below, the ciprofloxacin salt is ciprofloxacin hydrochloride monohydrate.

In a particular embodiment of the combination of the first aspect, optionally in combination with any of the embodiments provided above or below, the combination comprises ciprofloxacin hydrochloride and fluocinolone acetonide for use in the prevention and/or treatment of an ocular disease, wherein the prevention and/or treatment comprises the topical administration of the combination.

"Fluocinolone acetonide" refers to a compound with a CAS number 67-73-2 and of formula (II):

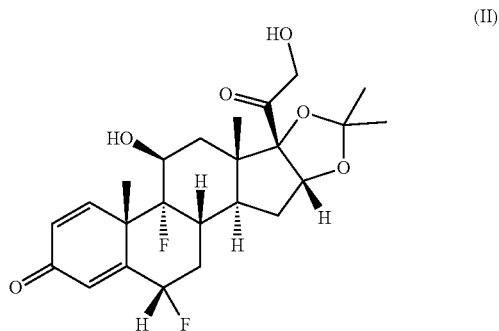

(II)

As disclosed before, in a fourth aspect the present invention provides an ophthalmic topical pharmaceutical composition comprising a therapeutically effective amount of ciprofloxacin, or a pharmaceutically acceptable salt thereof, and a therapeutically effective amount fluocinolone acetonide, together with at least one ophthalmically acceptable excipient, diluent, or carrier, for use in the prevention and/or treatment of an ocular disease, wherein the prevention and/or treatment comprises the topical administration of the composition.

The expression "therapeutically effective amount" as used herein, refers to the amount of ciprofloxacin or a pharmaceutically acceptable salt thereof, or fluocinolone acetonide that, when administered, is sufficient to prevent development of, or alleviate to some extent, one or more of the symptoms of the disease or condition which is addressed. The particular dose of ciprofloxacin and fluocinolone acetonide administered according to this invention will of course be determined by the particular circumstances surrounding the case, including the active compound administered, the route of administration, the particular condition being treated, and similar considerations.

The term "ophthalmically acceptable excipient, diluent, or carrier" refers to compounds, compositions, and/or solutions which are, within the scope of sound medical judgment, suitable specifically for contact with the tissues of the eye, and the area surrounding the eye without excessive toxicity, irritation, allergic response, or other problem complications commensurate with a reasonable benefit/risk ratio. They include, without limitation, surfactants, pH adjusting agents, preservatives, antioxidants, chelating agents, stabilizers, viscosity increasing agents, adhesive polymers, in situ gelling polymers, penetration enhancers, diluents and tonicity adjusting agents. Each component must be acceptable in the sense of being compatible with the other ingredients of the composition.

As used herein, the topical administration of the combination or the composition refers to the topical administration into the eye surface or the eyelid, particularly the inside of the eyelid. Topical ocular dosage forms for use according to the invention are those appropriated for allowing the active ingredients to be stable and to be applied topically onto the surface of eye (cornea, conjunctiva, lacrimal gland, and accessory lacrimal glands, meibomian glands, anterior sclera, iris, trabecular meshwork, or ciliary body) or eyelid and eyelashes with their associated glands of Moll and Zeiss.

In a particular embodiment of the first, second, third and fourth aspects, optionally in combination with any of the embodiments provided above or below, the fluocinolone acetonide enhances the tissue penetration of ciprofloxacin, or the pharmaceutically acceptable salt thereof.

In a particular embodiment of the first, second, third and fourth aspects, optionally in combination with any of the embodiments provided above or below, the prevention and/or treatment is preoperative or postoperative. As used herein, the term "preoperative" refers to the period prior to surgery, in particular ophthalmic surgery, and the term "postoperative" refers to the period after surgery, in particular ophthalmic surgery.

In a particular embodiment of the first, second, third and fourth aspects, optionally in combination with any of the embodiments provided above or below, the ocular disease is eye infection.

For the purpose of the present invention, the term "eye infection" as used herein refers to an infection caused by a microorganism or microorganisms in the eye structure and around the eye. Particularly, the term "eye structure" includes among others the inner surface of the eyelids and lacrimal apparatus, the meibomian glands, the tarsal crypts of Henle, the limbal glands of Manz, the conjunctiva, the cornea, the uvea, the aqueous humour, the iris, the vitreous body, the sclera, the lens, the choroid, the retina, and the optic nerve. And the term "around the eye" includes among others the eyelids and eyelashes with their associated glands of Moll and Zeiss, the tarsi and orbital septum, periorbital soft tissues, levator muscle, Müellers muscle, orbicularis muscle and submuscular areolar tissue. In an embodiment of the first, second, third and fourth aspects, optionally in combination with any of the embodiments provided above or below, the eye infection is an infection of the "eye structure" as defined above. In an embodiment of the first, second, third and fourth aspects, optionally in combination with any of the embodiments provided above or below, the eye infection is an infection of "around the eye" as defined above.

In a particular embodiment of the first, second, third and fourth aspects, optionally in combination with any of the embodiments provided above or below, the eye infection is bacterial eye infection. The eye infection can be caused by numerous genera of bacteria, including but not limited to, *Staphylococcus, Streptococcus, Treponema*, Pneumococcus, Gonococcus, *Haemophilus, Klebsiella, Neisseria, Chlamydia, Mycobacterium, Flavobacterium, Serratia, Propionibacterium, Acinetobacter, Escherichia, Proteus, Aeromonas, Providencia, Brucella, Salmonella, Campylobacter, Legionella, Moraxella, Shigella, Citrobacter, Morganella, Vibrio, Edwardsiella, Enterobacter, Pasteurella, Yersinia Actinomyces, Pseudomonas, Corynebacterium, Meningococcus, Pseudomonas, Haemophilus* and *Enterococcus*. The most relevant species of the *Staphylococcus* and *Streptococcus* genera are *Staphylococcus aureus, Staphylococcus epidermidis, Streptococcus viridans*, and *Streptococcus pneumoniae*.

In a particular embodiment of the first, second, third and fourth aspects, optionally in combination with any of the embodiments provided above or below, the eye infection is corneal ulcer caused by bacteria selected from the group consisting of *Pseudomonas aeruginosa, Serratia marcescens, Staphylococcus aureus, Staphylococcus epidermidis, Streptococcus pneumoniae, Streptococcus viridans*, and combinations thereof; or alternatively, conjunctivitis caused by bacteria selected from the group consisting of *Haemophilus influenzae, Staphylococcus aureus, Staphylococcus epidermidis, Streptococcus pneumoniae*, and combinations thereof.

In a particular embodiment of the first, second, third and fourth aspects, optionally in combination with any of the embodiments provided above or below, the eye infection is caused by facultative or obligate intracellular bacteria or antibiotic-resistant bacteria. "Antibiotic-resistant bacteria" refers to bacterial strains that have developed resistance to antibiotics due to genetic or non-genetic causes.

In a particular embodiment of the first, second, third and fourth aspects, optionally in combination with any of the embodiments provided above or below, the eye infection is selected from the group consisting of acute dacryocystitis, chronic dacryocystitis, blepharitis, blepharoconjunctivitis, angular blepharoconjunctivitis, contact blepharoconjunctivitis, seborrheic blepharoconjunctivitis, seborrheic blepharitis, Staphylococcal blepharitis, *demodex* blepharitis, pinkeye, epidemic conjunctivitis, inclusion conjunctivitis, inclusion blennorrhoea of the newborn, swimming pool conjunctivitis, ocular lymphogranuloma venereum, trachoma, viral conjunctivitis, conjunctival myiasis, keratoconjunctivitis, epidemic keratoconjunctivitis, hordeola (sties) and chalazia, infectious corneal ulcer, keratitis, epidemic keratitis, bacterial keratitis, fungal keratitis, herpetic keratitis, external and internal hordeolum (sty), ophthalmia neonatorum, orbital cellulitis, periorbital cellulitis, orbital abscess, vitritis, neuroretinitis, preseptal cellulitis, endophthalmitis, acute endophthalmitis after cataract surgery, uveitis, and combinations thereof.

In a particular embodiment of the first, second, third and fourth aspects, optionally in combination with any of the embodiments provided above or below, the eye infection is selected from the group consisting of acute dacryocystitis, chronic dacryocystitis, blepharitis, blepharoconjunctivitis, angular blepharoconjunctivitis, contact blepharoconjunctivitis, seborrheic blepharoconjunctivitis, seborrheic blepharitis, Staphylococcal blepharitis, *demodex* blepharitis, pinkeye, epidemic conjunctivitis, inclusion conjunctivitis, inclusion blennorrhoea of the newborn, swimming pool conjunctivitis, ocular lymphogranuloma venereum, trachoma, viral conjunctivitis, conjunctival myiasis, keratoconjunctivitis, epidemic keratoconjunctivitis, hordeola (sties) and chalazia, infectious corneal ulcer, keratitis, epidemic keratitis, bacterial keratitis, fungal keratitis, herpetic keratitis, external and internal hordeolum (sty), ophthalmia neonatorum, vitritis, neuroretinitis, endophthalmitis, acute endophthalmitis after cataract surgery, uveitis and combinations thereof.

In a more particular embodiment, the prevention and/or treatment is prophylactic treatment before or after ocular surgery.

In a particular embodiment of the first, second, third and fourth aspects, optionally in combination with any of the embodiments provided above or below, the prevention and/or treatment comprises administering a topical dose of ciprofloxacin, or a pharmaceutically acceptable salt thereof, from 0.01 mg/day to 30 mg/day, from 0.05 mg/day to 20 mg/day, from 0.1 mg/day to 10 mg/day, from 0.15 mg/day to 5 mg/day; from 0.2 mg/day to 4 mg/day, from 0.25 mg/day to 3 mg/day, from 0.3 mg/day to 2.5 mg/day, from 0.4 mg/day to 2 mg/day, from 0.45 mg/day to 1.9 mg/day, from 0.5 mg/day to 1.8 mg/day, from 0.6 mg/day to 1.7 mg/day, from 0.7 mg/day to 1.6 mg/day, from 0.8 mg/day to 1.5 mg/day, from 0.9 mg/day to 1.4 mg/day, from 0.95 mg/day to 1.3 mg/day, from 1 mg/day to 1.2 mg/day. More particularly, the prevention and/or treatment comprises administering a topical dose of ciprofloxacin, or a pharmaceutically acceptable salt thereof, from 0.115 mg/day to 0.23 mg/day, from 0.46 mg/day to 0.92 mg/day, or from 0.92 mg/day to 1.84 mg/day.

In a particular embodiment of the first, second, third and fourth aspects, optionally in combination with any of the embodiments provided above or below, ciprofloxacin or the pharmaceutically acceptable salt thereof is at a concentration from 0.1% to 0.8% w/v, from 0.2% to 0.6% w/v, from 0.3% to 0.4% w/v, or of 0.349%. More particularly, the pharmaceutically acceptable salt of ciprofloxacin is ciprofloxacin hydrochloride monohydrate.

In a particular embodiment of the first, second, third and fourth aspects, optionally in combination with any of the embodiments provided above or below, fluocinolone acetonide is at a concentration from 0.01% to 0.10% w/v, from 0.015% to 0.05% w/v, from 0.02% to 0.03% w/v, or of 0.025% w/v.

In a particular embodiment of the first, second, third and fourth aspects, optionally in combination with any of the embodiments provided above or below, ciprofloxacin or the pharmaceutically acceptable salt thereof is at a concentration from 0.1% to 0.8% w/v and fluocinolone acetonide is at a concentration from 0.01% to 0.10% w/v. In an even more particular embodiment, ciprofloxacin or the pharmaceutically acceptable salt thereof is at a concentration of 0.349% and fluocinolone acetonide is at a concentration of 0.025% w/v. More particularly, the pharmaceutically acceptable salt of ciprofloxacin is ciprofloxacin hydrochloride monohydrate.

In a particular embodiment of the first, second, third and fourth aspects, optionally in combination with any of the embodiments provided above or below, the weight ratio between ciprofloxacin, or the pharmaceutically acceptable salt thereof, and fluocinolone acetonide is higher than or equal to 1:0.01; higher than or equal to 1:0.02; higher than or equal to 1:0.03; higher than or equal to 1:0.04; higher than or equal to 1:0.05; higher than or equal to 1:0.06; or higher than or equal to 1:0.07. More particularly, the pharmaceutically acceptable salt of ciprofloxacin is ciprofloxacin hydrochloride monohydrate.

In a particular embodiment of the first, second, third and fourth aspects, optionally in combination with any of the embodiments provided above or below, the weight ratio between ciprofloxacin, or the pharmaceutically acceptable salt thereof, and fluocinolone acetonide is from 1:0.01 to 1:3; from 1:0.02 to 1:2.5; from 1:0.03 to 1:2.25. Even more particularly, the weight ratio between ciprofloxacin, or the pharmaceutically acceptable salt thereof, and fluocinolone acetonide is from 1:0.04 to 1:2.24; from 1:0.05 to 1:1.12; from 1:0.051 to 1:0.56; from 1:0.052 to 1:0.28, from 1:0.055 to 1:0.14, from 1:0.057 to 1:0.13, from 1:0.06 to 1:0.12, from 1:0.065 to 1:0.11, or from 1:0.07 to 1:0.10. More particularly, the pharmaceutically acceptable salt of ciprofloxacin is ciprofloxacin hydrochloride monohydrate.

In a particular embodiment of the fourth aspect, optionally in combination with any of the embodiments provided above or below, the composition is formulated for the release of ciprofloxacin, or a pharmaceutically acceptable salt thereof, and fluocinolone acetonide, from 1 to 2 days. More particularly, the composition is formulated for the release of ciprofloxacin, or a pharmaceutically acceptable salt thereof, and fluocinolone acetonide up to 48 hours.

In a particular embodiment of the fourth aspect, optionally in combination with any of the embodiments provided above or below, the at least one ophthalmically acceptable excipient, diluent, or carrier comprises a non-ionic surfactant. In a more particular embodiment, the non-ionic surfactant has a hydrophilic-lipophilic balance (HLB) value from 10 to 18, most preferable from 14 to 18. Pharmaceutically acceptable examples of non-ionic surfactants with a HLB value between 14 and 18 include but are not limited to sorbitan polyoxyethylene fatty acid derivatives; polyoxyethylene hydrogenated castor oil derivatives; polyoxyethylene fatty acid derivatives, polyoxyethylene-polyoxypropylene co-polymers and block-co-polymers.

The term "surfactant", as used herein, refers to a compound that lowers the surface tension or interfacial tension between two liquids or between a liquid and a solid.

Surfactants have a hydrophobic part and a hydrophilic part. Depending on the nature of the hydrophilic part the surfactants are classified as non-ionic (surfactant with a non-charged but polar hydrophilic part), anionic (when the hydrophilic part contains a negatively charged group), cationic (when the hydrophilic part contains a positively charged group) or amphoteric (when the hydrophilic part contains both cationic and anionic groups).

The term "hydrophilic-lipophilic balance" or "HLB" refers to the ratio of the hydrophilicity of the polar groups of the surface-active molecules to the hydrophobicity of the lipophilic part of the same molecules.

In a more particular embodiment of the fourth aspect, optionally in combination with any of the embodiments provided above or below, the non-ionic surfactant is selected from the group consisting of sorbitan polyoxyethylene fatty acid derivatives such as Polysorbate 20 (polyoxyethylene (20) sorbitan monolaurate), Polysorbate 40 (polyoxyethylene (20) sorbitan monopalmitate), Polysorbate 60 (polyoxyethylene (20) sorbitan monostearate) and Polysorbate 80

(polyoxyethylene (20) sorbitan monooleate); polyoxyethylene Hydrogenated castor oil derivatives such as polyoxyethylene (60) hydrogenated castor oil, polyoxyethylene glycol (60) hydrogenated castor oil and polyoxyethylene glycol (40) hydrogenated castor oil; polyoxyethylene fatty acid derivatives such as polyoxyethylene (20) stearate, polyoxyethylene (32) distearate, polyoxyethylene (20) oleate, olyoxyethylene (32) oleate and polyoxyethylene (32) dioleate; fatty alcohol ethoxylates such as polyoxyethylene (20) oleyl alcohol, polyoxyethylene (20) stearyl alcohol and polyoxyethylene (20) cetearyl alcohol, polyoxyethylene-polyoxypropylene co-polymers and block-co-polymers, and mixtures thereof. In a preferred embodiment the non-ionic surfactant is Polysorbate. In an even more particular embodiment, the non-ionic surfactant is Polysorbate 80.

In a more particular embodiment of the fourth aspect, optionally in combination with any of the embodiments provided above or below, the non-ionic surfactant is at a concentration from 0.05% to 10%, or more particularly, from 0.5% to 4.0% w/v.

In a particular embodiment of the fourth aspect, optionally in combination with any of the embodiments provided above or below, the at least one ophthalmically acceptable excipient, diluent, or carrier further comprises a tonicity adjusting agent.

As used herein, "tonicity adjusting agent" refers to any agent that alters the osmolality of an aqueous solution. Typically, tonicity agents are used to adjust the osmolality of a solution to bring it closer to the osmotic pressure of body fluids.

In a more particular embodiment of the fourth aspect, optionally in combination with any of the embodiments provided above or below, the tonicity adjusting agent is selected from the group consisting of dextrose, glycerin, sorbitol, mannitol, xylitol, polyethylene glycol, propylene glycol, dextran, potassium chloride, sodium chloride, calcium chloride, sodium phosphate, potassium phosphate, sodium bicarbonate, calcium carbonate, sodium lactate, and mixtures thereof. More particularly, the tonicity adjusting agent is glycerin.

In a more particular embodiment of the fourth aspect, optionally in combination with any of the embodiments provided above or below, the tonicity adjusting agent is at a concentration from 0.05% to 10%, or more particularly, from 0.5% to 4.0% w/v.

In a particular embodiment of the fourth aspect, optionally in combination with any of the embodiments provided above or below, the at least one ophthalmically acceptable excipient, diluent, or carrier further comprises a viscosity increasing agent.

In the context of the present disclosure, a "viscosity increasing agent" refers to any agent which increases the viscosity of the aqueous solution into which it has been added.

In a particular embodiment of the fourth aspect, optionally in combination with any of the embodiments provided above or below, the viscosity increasing agent is selected from the group consisting of polyvinylpyrrolidone, such as Povidone K 25, Povidone K 30 and Povidone K 90F; polyvinyl alcohol, xanthan gum, guar gum, welan gum, tragacanth gum, *ceratonia* gum, agar, methylcellulose, ethylcellulose, hydroxyethyl cellulose, hydroxyethylmethyl cellulose, hydroxypropyl cellulose, hydroxypropylmethyl cellulose, sodium carboxymethylcellulose, calcium carboxymethylcellulose, polyethylene glycol, glycerin, carrageenan, sodium alginate, potassium alginate, propylene glycol alginate, sodium hyaluronate, carbomers and maltodextrin. In a preferred embodiment the viscosity increasing agent is a polyvinylpyrrolidone selected from Povidone K 25, Povidone K 30, and Povidone K 90F. In a particularly preferred embodiment, the viscosity increasing agent is Povidone K 90F.

In a more particular embodiment of the composition of the fourth aspect, optionally in combination with any of the embodiments provided above or below, the viscosity increasing agent is at a concentration from 0.01% to 5%, or more particularly, from 0.05% to 1.00% w/v.

In a particular embodiment of the fourth aspect, optionally in combination with any of the embodiments provided above or below, the at least one ophthalmically acceptable excipient, diluent, or carrier further comprises an ophthalmically acceptable pH adjusting agent.

In a particular embodiment of the fourth aspect, optionally in combination with any of the embodiments provided above or below, the composition has a pH from 3.5 to 8.5, more in particular from 4.0 to 7.5.

The term "pH" is defined as the value given by a suitable, properly standardized, potentiometric sensor and measuring system. The measuring system has traditionally been referred to as the "pH meter". The pH of the compositions is measured by compendial traditional methods.

The term "pH adjusting agent" refers to acids or bases or their mixtures that can be used to adjust the pH of the finished product to the desired level.

In an embodiment, optionally in combination with any of the embodiments provided above or below, the composition of the invention further comprises a pH adjusting agent selected from the group consisting of lactic acid and salts thereof (such as sodium lactate, potassium lactate and calcium lactate), citric acid and salts thereof (such as sodium citrate, potassium citrate, calcium citrate, lithium citrate, trisodium citrate and disodium hydrogen citrate), tartaric acid and salts thereof (such as sodium tartrate potassium tartrate, calcium tartrate and lithium tartrate), acetic acid and salts thereof (such as sodium acetate, potassium acetate and calcium acetate), hydrochloric acid, boric acid and salts thereof (sodium borate), sulphuric acid and salts thereof (such as sodium sulphate and potassium sulphate), nitric acid, hydrochloric acid, phosphoric acid and salts thereof (such as sodium dihydrogen phosphate, sodium monohydrogen phosphate, potassium dihydrogen phosphate lithium phosphate, potassium phosphate and calcium phosphate), carbonic acid and salts thereof (such as sodium carbonate, sodium hydrogen carbonate and potassium hydrogen carbonate), maleic acid and salts thereof (lithium maleate, sodium maleate, potassium maleate and calcium maleate), succinic acid and salts thereof (lithium succinate, sodium succinate, potassium succinate and calcium succinate), sodium hydroxide, potassium hydroxide, triethanolamine, diisopropanolamine, ammonia, tris(hydroxymethyl)aminomethane, tris(hydroxymethyl)aminomethane hydrochloride, and mixtures thereof. In another embodiment, the pH adjusting agent is selected from the group consisting of tris(hydroxymethyl)aminomethane, tris(hydroxymethyl) aminomethane hydrochloride, potassium dihydrogen phosphate, disodium hydrogen phosphate, and mixtures thereof.

In a particular embodiment of the fourth aspect, optionally in combination with any of the embodiments provided above or below, the ophthalmic topical pharmaceutical composition comprises the following ingredients, in w/v percentages:

(i) from 0.01% to 0.10% of fluocinolone acetonide accompanied by from 0.1% to 0.8% of ciprofloxacin or a pharmaceutically acceptable salt thereof;

(ii) from 0.05% to 10% of one or more pharmaceutically acceptable non-ionic surfactants with a hydrophilic-lipophilic balance (HLB) value from 10 to 18;

(iii) from 0.05% to 10% of one or more pharmaceutically acceptable tonicity adjusting agents;

(iv) from 0.01% to 5% of one or more pharmaceutically acceptable viscosity increasing agents;

(v) optionally, an amount of one or more pharmaceutically acceptable pH adjusting agents in q.s. to adjust pH 3.5-8.5; and (vi) water.

In a particular embodiment of the fourth aspect, optionally in combination with any of the embodiments provided above or below, the ophthalmic topical pharmaceutical composition comprises the following ingredients: from 0.02% w/v to 0.03% w/v of fluocinolone acetonide, from 0.2% to 0.4% w/v of ciprofloxacin or a pharmaceutically acceptable salt thereof; from 1% to 7% w/v of Polysorbate 80; from 2% to 3% w/v of glycerin; from 0.1% to 0.6% w/v of Povidone K 90F; optionally, one or more pharmaceutically acceptable pH adjusting agent; and water. In a preferred embodiment the composition consists exclusively of the above-mentioned ingredients.

With the aim of making such compositions easy to be administered by the patient, and also to avoid disturbance of vision as much as possible when the compositions are applied, the compositions are preferably in the form of eye drop solutions, more in particular eye drop transparent solutions. Thus, in a particular embodiment of the fourth aspect, optionally in combination with any of the embodiments provided above or below, the ophthalmic topical pharmaceutical composition is in the form of eye drop, eye mist, eye ointment, or eye gel. In a more particular embodiment, the form of eye drop is sterilized and contained in disposable single-dose eye drop containers for ophthalmic use. This form is advantageous because these compositions do not require the inclusion of preservatives in the composition.

The term "sterile" refers to a composition that has been aseptically processed and that is devoid of viable bacteria, fungi, or other microorganisms.

Ophthalmic topical pharmaceutical compositions of the present invention can be prepared according to methods well known in the state of the art. The appropriate excipients and/or carriers, as well as any pH adjusting agents, and their amounts, can readily be determined by those skilled in the art according to the type of formulation being prepared.

In a particular embodiment of the fourth aspect, the composition is for immediate release of ciprofloxacin, or a pharmaceutically acceptable salt thereof, and fluocinolone acetonide. These types of formulations allow a quick release of the active ingredient serving for the purpose of rapidly acting on the different tissues of the eye.

On the alternative and in another particular embodiment of the fourth aspect, the ophthalmic topical pharmaceutical composition for use as defined above is a composition for the controlled along time release of the active principle, also termed modified-release composition or dosage forms. In particular, it is for the release of the active principle from 1 to 2 days. More particularly, it is for the release of the active principle from 1 to 2 days and is formulated for administration to a subject up to once a day or once every two days.

These compositions allow reducing the administration times and promote a simpler posology. Examples of these non-immediate release compositions, in which active principle is released during a period of time, comprise sustained-release compositions and prolonged release compositions. Sustained-release dosage forms are dosage forms designed to release (liberate) a drug at a predetermined rate in order to maintain a constant drug concentration for a specific period of time with minimum side effects. This can be achieved through a variety of formulations, including drug-polymer conjugates. Prolonged release compositions are compositions in which the drug is delivered within a period of time (extended-release usually at a constant rate) or to a specific target in the body (targeted-release dosage).

For "release from 1 to 2 days", is to be understood when related to any of the aspects or embodiments of the invention, that the release of ciprofloxacin, or a pharmaceutically acceptable salt thereof, and fluocinolone acetonide, is accomplished in such a way that at least 85% of the active principle in the formulation has been released from the administration day to whatever day is the indicated for such formulation (e.g. 1 or 2). That is, an ophthalmic topical pharmaceutical composition formulated for the release of the active principle in 2 days, means that at least 85%, more in particular 90%, and even more in particular 100% of the active principle has been released at day 2. The skilled man in the art of topical eye compositions will know the standard protocols for determining the release percentages of the active principle.

In another particular embodiment of the fourth aspect of the invention, the ophthalmic topical pharmaceutical compositions for use as disclosed above is formulated for administration to a subject, in particular a mammal, and more in particular a human, once or twice per eye every 0.25, 0.5, 1, 2, 4, 6, 8, 12, 16, 24 and 48 hours. More particularly, the ophthalmic topical pharmaceutical compositions are for immediate release and is formulated for administration to a subject, in particular a mammal, and more in particular a human, once or twice per eye every 0.25, 0.5, 1, 2, 4, 6, 8, 12, 16, and 24.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim and shall not be construed as limiting the scope of the claim. Furthermore, the present invention covers all possible combinations of particular and preferred embodiments described herein.

For reasons of completeness, various aspects of the invention are set out in the following numbered clauses:

Clause 1. A combination comprising ciprofloxacin, or a pharmaceutically acceptable salt thereof, and fluocinolone acetonide for use in the prevention and/or treatment of an ocular disease, wherein the prevention and/or treatment comprises the topical administration of the combination.

Clause 2. The combination for use according to clause 1, wherein the prevention and/or treatment of an ocular disease comprises the topical administration to a subject of:

(a) an ophthalmic topical pharmaceutical composition comprising:

a therapeutically effective amount of ciprofloxacin, or a pharmaceutically acceptable salt thereof; and a therapeutically effective amount of fluocinolone acetonide;

together with one or more ophthalmically acceptable excipients, diluents, or carriers; or alternatively, (b) simultaneously, sequentially, or separately:

(b1) an ophthalmic topical pharmaceutical composition comprising a therapeutically effective amount of ciprofloxacin, or a pharmaceutically acceptable salt thereof; together with one or more pharmaceutically acceptable excipients, diluents, or carriers; and (b2) an ophthalmic topical pharmaceutical composition comprising a therapeutically effective amount of fluocinolone acetonide together with one or more ophthalmically acceptable excipients, diluents, or carriers.

Clause 3. Ciprofloxacin, or a pharmaceutically acceptable salt thereof, for use in the prevention and/or treatment of an ocular disease by topical administration, wherein the ciprofloxacin, or the pharmaceutically acceptable salt thereof, is for use in combination therapy with fluocinolone acetonide.

Clause 4. Fluocinolone acetonide for use in the prevention and/or treatment of an ocular disease by topical administration, wherein the fluocinolone acetonide is for use in combination therapy with ciprofloxacin, or a pharmaceutically acceptable salt thereof.

Clause 5. An ophthalmic topical pharmaceutical composition comprising a therapeutically effective amount of ciprofloxacin, or a pharmaceutically acceptable salt thereof, and a therapeutically effective amount of fluocinolone acetonide, together with at least one ophthalmically acceptable excipient, diluent, or carrier, for use in the prevention and/or treatment of an ocular disease, wherein the prevention and/or treatment comprises the topical administration of the composition.

Clause 6. The combination for use according to any of clauses 1-2, or the ophthalmic topical pharmaceutical composition for use according to clause 5, wherein the ciprofloxacin salt is ciprofloxacin hydrochloride.

Clause 7. The combination for use according to any of clauses 1-2 and 6, or the ophthalmic topical pharmaceutical composition for use according to any of clauses 5-6, wherein the ocular disease is eye infection.

Clause 8. The combination or the ophthalmic topical pharmaceutical composition for use according to clause 7, wherein the eye infection is selected from the group consisting of acute dacryocystitis, chronic dacryocystitis, blepharitis, blepharoconjunctivitis, angular blepharoconjunctivitis, contact blepharoconjunctivitis, seborrheic blepharoconjunctivitis, seborrheic blepharitis, Staphylococcal blepharitis, *demodex* blepharitis, pinkeye, epidemic conjunctivitis, inclusion conjunctivitis, inclusion blennorrhoea of the newborn, swimming pool conjunctivitis, ocular lymphogranuloma venereum, trachoma, viral conjunctivitis, conjunctival myiasis, keratoconjunctivitis, epidemic keratoconjunctivitis, hordeola (sties) and chalazia, infectious corneal ulcer, keratitis, epidemic keratitis, bacterial keratitis, fungal keratitis, herpetic keratitis, external and internal hordeolum (sty), ophthalmia neonatorum, orbital cellulitis, periorbital cellulitis, orbital abscess, vitritis, neuroretinitis, preseptal cellulitis, endophthalmitis, acute endophthalmitis after cataract surgery, uveitis, and combinations thereof; preferably, the eye infection is selected from the group consisting of acute dacryocystitis, chronic dacryocystitis, blepharitis, blepharoconjunctivitis, angular blepharoconjunctivitis, contact blepharoconjunctivitis, seborrheic blepharoconjunctivitis, seborrheic blepharitis, Staphylococcal blepharitis, *demodex* blepharitis, pinkeye, epidemic conjunctivitis, inclusion conjunctivitis, inclusion blennorrhoea of the newborn, swimming pool conjunctivitis, ocular lymphogranuloma venereum, trachoma, viral conjunctivitis, conjunctival myiasis, keratoconjunctivitis, epidemic keratoconjunctivitis, hordeola (sties) and chalazia, infectious corneal ulcer, keratitis, epidemic keratitis, bacterial keratitis, fungal keratitis, herpetic keratitis, external and internal hordeolum (sty), ophthalmia neonatorum, vitritis, neuroretinitis, endophthalmitis, acute endophthalmitis after cataract surgery, uveitis, and combinations thereof.

Clause 9. The combination or the ophthalmic topical pharmaceutical composition for use according to clause 8, wherein the eye infection is caused by antibiotic-resistant bacteria.

Clause 10. The ophthalmic topical pharmaceutical composition for use according to any of clauses 5-9, wherein the ciprofloxacin or the pharmaceutically acceptable salt thereof is at a concentration from 0.1% to 0.8% w/v and the fluocinolone acetonide is at a concentration from 0.01% to 0.10% w/v.

Clause 11. The ophthalmic topical pharmaceutical composition for use according to any of clauses 5-10, wherein the weight ratio between the ciprofloxacin, or the pharmaceutically acceptable salt thereof, and the fluocinolone acetonide is higher than or equal to 1:0.01.

Clause 12. The ophthalmic topical pharmaceutical composition for use according to clause 11, wherein the weight ratio between the ciprofloxacin, or the pharmaceutically acceptable salt thereof, and the fluocinolone acetonide is from 1:0.04 to 1:3.

Clause 13. The ophthalmic topical pharmaceutical composition for use according to any of clauses 5-12, wherein the at least one ophthalmically acceptable excipient, diluent, or carrier comprises:

a non-ionic surfactant with a hydrophilic-lipophilic balance (HLB) value from 10 to18;
a tonicity adjusting agent;
a viscosity increasing agent;
a pH adjusting agent; or
mixtures thereof.

Clause 14. The ophthalmic topical pharmaceutical composition for use according to any of clauses 5-13, wherein the composition has a pH from 3.5 to 8.5.

Clause 15. The ophthalmic topical pharmaceutical composition for use according to any of clauses 5-14, wherein the composition is in the form of eye drop and it is contained in disposable single-dose eye drop containers for ophthalmic use.

Example: Intracellular Amounts of Ciprofloxacin in Presence of Different Corticosteroids Material and Methods Permeability assays were performed in triplicate and repeated at least in three independent assays on different days. For this purpose, SIRC (Statens Serum Institut Rabbit Cornea, ATCC® CCL-60™) cells were seeded in sterile 6-well microfilter plates and maintained in culture until confluence. SIRC cells were cultured in Eagle's Minimum Essential Medium (EMEM) supplemented with 10% foetal bovine serum (FBS) and with 1% of penicillin-streptomycin solution at 37° C. and 10% $CO_2$ in air. Ciprofloxacin was dissolved in dimethyl sulfoxide (DMSO) to prepare a concentrated stock solution which was further diluted in culture medium to obtain a final concentration of 20 μg/ml. Fluocinolone acetonide, dexamethasone or hydrocortisone sodium phosphate was as well dissolved in DMSO and diluted in the culture medium to obtain different concentrations of the corticosteroid in the cellular supernatant (0 µg/ml, 2.8 µg/ml, 5.6 µg/ml, 11.2 µg/ml, 22.4 µg/ml, and 44.8 µg/ml).

The cells were treated with ciprofloxacin alone or in combination with the different concentrations of each corticosteroid for 15 minutes. After the incubation period, the culture medium was removed, and the cells were harvested by trypsinization and centrifuged at 980 g for 5 min at 4° C. The cellular pellet was washed with saline solution to remove possible traces of residual extracellular compounds, centrifuged, and preserved at −80° C. for further analysis.

Intracellular ciprofloxacin was quantified by ultra-high-performance liquid chromatography coupled to tandem mass spectrometry (UHPLC-MS/MS). Previously to the instrumental analysis, cellular pellets were processed by adding acetonitrile/water (volume ratio 1:1). Chromatographic separation was carried out using an Acquity BEH C18 column (1.7 µm, 50×2.1 mm). Mobile phase consisted of a gradient using 0.1% formic acid in water and acetonitrile from 10% to 100% of the organic solvent in 6 min at a flow rate of 0.6 ml/min. The column was kept at 50° C., and 1 µl of sample was injected. Regarding the mass spectrometric detection, electrospray ionization in positive ion mode and Multiple Reaction Monitoring (MRM) acquisition were used. Transition monitored for ciprofloxacin was m/z 332.2→288.2, with cone voltage 35 V and collision energy 20 eV.

Results

Figure 2:
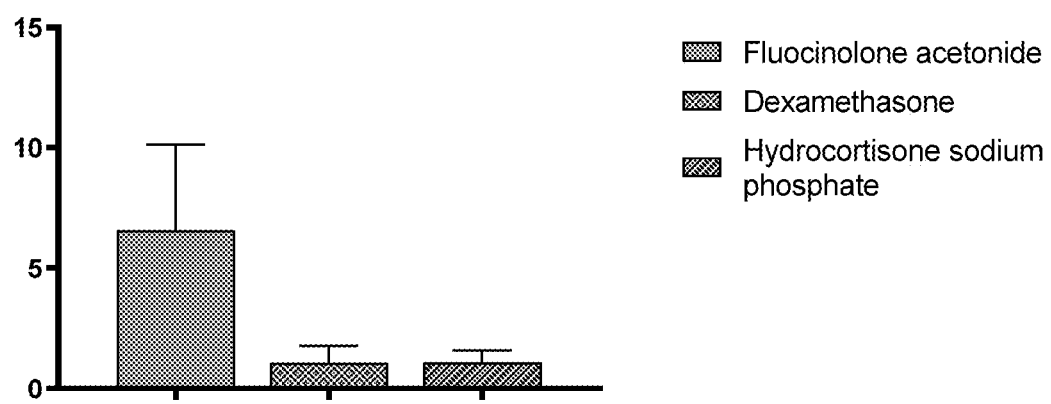
FIG. 2 shows the intracellular concentration of ciprofloxacin (ng/ml) in corneal epithelial cells, determined by ultra-high-performance liquid chromatography coupled to tandem mass spectrometry (UHPLC-MS/MS), following 15 minutes of incubation with different corticosteroids at 5.6 µg/ml and ciprofloxacin at 20 µg/ml. Data was normalized to the control sample (intracellular levels of ciprofloxacin in the absence of corticosteroids) by subtracting for each assay the value of the control. Results are expressed as means±S.E.M of three independent experiments. The y-axis represents the intracellular concentration of ciprofloxacin (ng/ml), and the x-axis represents the tested corticosteroid at 5.6 µg/ml.
Figure 3:
FIG. 3 shows the intracellular concentration of ciprofloxacin (ng/ml) in corneal epithelial cells, determined by ultra-high-performance liquid chromatography coupled to tandem mass spectrometry (UHPLC-MS/MS), following 15 minutes of incubation with different corticosteroids at 11.2 µg/ml and ciprofloxacin at 20 µg/ml. Data was normalized to the control sample (intracellular levels of ciprofloxacin in the absence of corticosteroids) by subtracting for each assay the value of the control. Results are expressed as means±S.E.M of three independent experiments. The y-axis represents the intracellular concentration of ciprofloxacin (ng/ml), and the x-axis represents the tested corticosteroid at 11.2 µg/ml.
Figure 4:
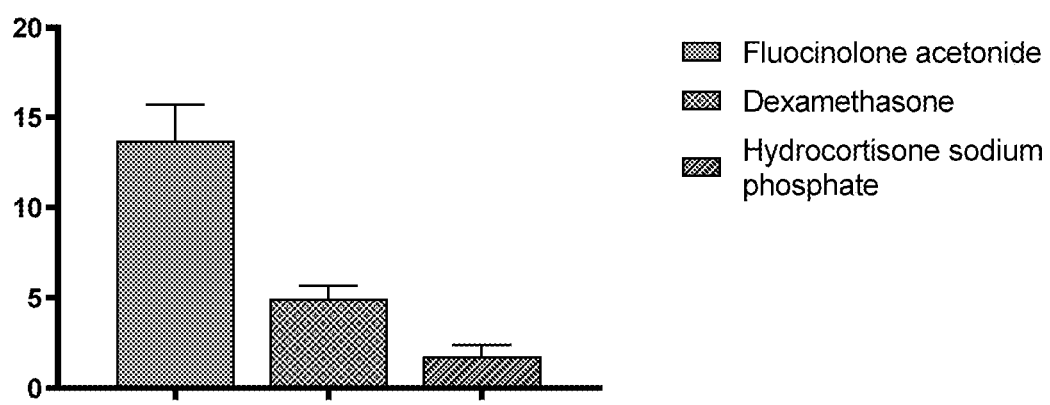
FIG. 4 shows the intracellular concentration of ciprofloxacin (ng/ml) in corneal epithelial cells, determined by ultra-high-performance liquid chromatography coupled to tandem mass spectrometry (UHPLC-MS/MS), following 15 minutes of incubation with different corticosteroids at 22.4 µg/ml and ciprofloxacin at 20 µg/ml. Data was normalized to the control sample (intracellular levels of ciprofloxacin in the absence of corticosteroids) by subtracting for each assay the value of the control. Results are expressed as means±S.E.M of three independent experiments. The y-axis represents the intracellular concentration of ciprofloxacin (ng/ml), and the x-axis represents the tested corticosteroid at 22.4 µg/ml.
Figure 5:
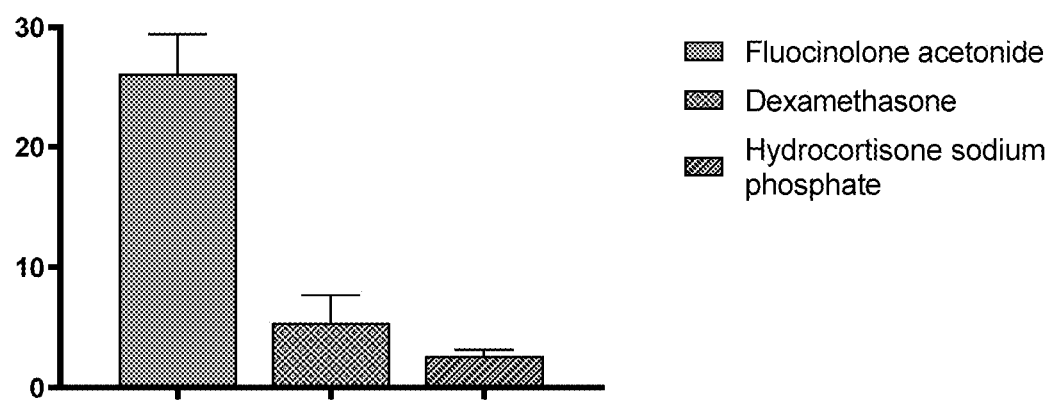
FIG. 5 shows the corrected intracellular concentration of ciprofloxacin (ng/ml) in corneal epithelial cells, determined by ultra-high-performance liquid chromatography coupled to tandem mass spectrometry (UHPLC-MS/MS), following 15 minutes of incubation with different corticosteroids at 44.8 µg/ml and ciprofloxacin at 20 µg/ml. Data was normalized to the control sample (intracellular levels of ciprofloxacin in the absence of corticosteroids) by subtracting for each assay the value of the control. Results are expressed as means±S.E.M of three independent experiments. The y-axis represents the intracellular concentration of ciprofloxacin (ng/ml), and the x-axis represents the tested corticosteroid at 44.8 µg/ml.

The intracellular concentration of ciprofloxacin increased in the presence of increasing concentrations of fluocinolone acetonide in the cell culture supernatant, although the concentration of the antibiotic in the supernatant was constant. This penetration enhancing effect was dose-dependent, considering that the higher the concentration of fluocinolone acetonide added, the higher the concentration of intracellular ciprofloxacin detected. This effect could be attributed to the unexpected high intracellular permeability of ciprofloxacin due to the presence of fluocinolone acetonide. In contrast, when dexamethasone or hydrocortisone sodium phosphate was added to the cell supernatant, intracellular levels of ciprofloxacin were lower than those observed in the presence of fluocinolone acetonide for all concentrations tested. In addition, constant intracellular concentrations of ciprofloxacin were observed at increasing concentrations in the cell culture supernatant for either dexamethasone or hydrocortisone sodium phosphate, indicating that neither of the two corticosteroids altered the uptake of ciprofloxacin into the cells (FIG. 1 to FIG. 5).

In summary, fluocinolone acetonide promotes the penetration of the antibiotic, increasing ciprofloxacin concentration in the intracellular compartment; meanwhile this positive effect cannot be associated to two of the most common ophthalmic corticosteroids (dexamethasone and hydrocortisone sodium phosphate). The combination of ciprofloxacin and fluocinolone acetonide is an innovative strategy for the treatment of ocular infections.

CITATION LIST

Fleiszig S. M. et al, "*Pseudomonas aeruginosa* invades corneal epithelial cells during experimental infection", Infect Immun, 1994, vol. 62(8), pp. 3485-93.

Kadmiel M. et al., "Glucocorticoid action in human corneal epithelial cells establishes roles for corticosteroids in wound healing and barrier function of the eye", Exp Eye Res., 2016, vol. 152, pp. 10-33.

The invention claimed is:

1. A method for treating an ocular bacterial infection, the method comprising topical ophthalmic administration of a combination comprising ciprofloxacin, or a pharmaceutically acceptable salt thereof, and fluocinolone acetonide to a subject in need thereof.

2. The method according to claim 1, wherein the treatment of an ocular bacterial infection comprises the topical ophthalmic administration to a subject of:
   (a) an ophthalmic topical pharmaceutical composition comprising:
      a therapeutically effective amount of ciprofloxacin, or a pharmaceutically acceptable salt thereof; and
      a therapeutically effective amount of fluocinolone acetonide;
      together with one or more ophthalmically acceptable excipients, diluents, or carriers;
   or alternatively,
   (b) simultaneously, sequentially, or separately:
      (b1) an ophthalmic topical pharmaceutical composition comprising a therapeutically effective amount of ciprofloxacin, or a pharmaceutically acceptable salt thereof; together with one or more pharmaceutically acceptable excipients, diluents, or carriers; and
      (b2) an ophthalmic topical pharmaceutical composition comprising a therapeutically effective amount of fluocinolone acetonide together with one or more ophthalmically acceptable excipients, diluents, or carriers.

3. A method for treating an ocular bacterial infection in a subject in need thereof, the method comprising topical ophthalmic administration of an ophthalmic topical pharmaceutical composition comprising a therapeutically effective amount of ciprofloxacin, or a pharmaceutically acceptable salt thereof, and a therapeutically effective amount of fluocinolone acetonide, together with at least one ophthalmically acceptable excipient, diluent, or carrier.

4. The method according to claim 1, wherein the ciprofloxacin salt is ciprofloxacin hydrochloride.

5. The method according to claim 1, wherein the ocular bacterial infection is selected from the group consisting of acute dacryocystitis, chronic dacryocystitis, blepharitis, blepharoconjunctivitis, angular blepharoconjunctivitis, contact blepharoconjunctivitis, seborrheic blepharoconjunctivitis, seborrheic blepharitis, Staphylococcal blepharitis, *demodex* blepharitis, pinkeye, epidemic conjunctivitis, inclusion conjunctivitis, inclusion blennorrhoea of the newborn, swimming pool conjunctivitis, ocular lymphogranuloma venereum, trachoma, viral conjunctivitis, conjunctival myiasis, keratoconjunctivitis, epidemic keratoconjunctivitis, hordeola (sties) and chalazia, infectious corneal ulcer, keratitis, epidemic keratitis, bacterial keratitis, fungal keratitis, herpetic keratitis, external and internal hordeolum (sty), ophthalmia neonatorum, orbital cellulitis, periorbital cellulitis, orbital abscess, vitritis, neuroretinitis, preseptal cellulitis, endophthalmitis, acute endophthalmitis after cataract surgery, uveitis, and combinations thereof.

6. The method according to claim 5, wherein the ocular bacterial infection is caused by antibiotic-resistant bacteria.

7. The method according to claim 3, wherein the ciprofloxacin or the pharmaceutically acceptable salt thereof is at a concentration from 0.1% to 0.8% w/v and the fluocinolone acetonide is at a concentration from 0.01% to 0.10% w/v.

8. The method according to claim 3, wherein the weight ratio between the ciprofloxacin, or the pharmaceutically acceptable salt thereof, and the fluocinolone acetonide is higher than or equal to 1:0.01.

9. The method according to claim 8, wherein the weight ratio between the ciprofloxacin, or the pharmaceutically acceptable salt thereof, and the fluocinolone acetonide is from 1:0.04 to 1:3.

10. The method according to claim 3, wherein the at least one ophthalmically acceptable excipient, diluent, or carrier comprises:
   a non-ionic surfactant with a hydrophilic-lipophilic balance (HLB) value from 10 to 18;
   a tonicity adjusting agent;
   a viscosity increasing agent;
   a pH adjusting agent; or
   mixtures thereof.

11. The method according to claim 3, wherein the composition has a pH from 3.5 to 8.5.

12. The method according to claim 3, wherein the composition is in the form of eye drop and it is contained in disposable single-dose eye drop containers for ophthalmic use.

13. The method according to claim 1, wherein the topical ophthalmic administration comprises administering into an eye surface or an eyelid of the subject in need thereof.

14. A method for increasing intracellular concentration of ciprofloxacin in corneal epithelial cells in an eye of a subject, the method comprising: topically administering a combination comprising ciprofloxacin, or a pharmaceutically acceptable salt thereof, and fluocinolone acetonide to the eye of the subject.

* * * * *